United States Patent
Reif et al.

(10) Patent No.: US 7,279,602 B2
(45) Date of Patent: Oct. 9, 2007

(54) METHOD FOR SEPARATING TRIETHANOLAMIN FROM A MIXTURE OBTAINABLE BY AMMONIA AND ETHYLENE OXIDE REACTION

(75) Inventors: Wolfgang Reif, Frankenthal (DE); Hans Hammer, Mannheim (DE); Guenther Ruider, Wachenheim (DE); Anton Meier, Birkenheide (DE); Philip Buskens, Hoogstraten (BE); Matthias Frauenkron, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 16 days.

(21) Appl. No.: 10/573,498

(22) PCT Filed: Oct. 2, 2004

(86) PCT No.: PCT/EP2004/011022

§ 371 (c)(1),
(2), (4) Date: Mar. 27, 2006

(87) PCT Pub. No.: WO2005/035481

PCT Pub. Date: Apr. 21, 2005

(65) Prior Publication Data

US 2006/0293541 A1    Dec. 28, 2006

(30) Foreign Application Priority Data

Oct. 8, 2003    (DE) ................................ 103 46 779

(51) Int. Cl.
*C07C 209/84* (2006.01)
*C07C 209/86* (2006.01)

(52) U.S. Cl. ...................... 564/499; 564/475; 564/477

(58) Field of Classification Search ................. 564/499
See application file for complete search history.

(56) References Cited

U.S. PATENT DOCUMENTS

| 1,968,512 | A | * | 7/1934 | Young ......................... 203/91 |
| 3,453,183 | A | | 7/1969 | Okubo et al. |
| 3,742,059 | A | | 6/1973 | Dowd |
| 3,849,262 | A | * | 11/1974 | Cocuzza ...................... 203/38 |
| 4,381,223 | A | * | 4/1983 | Gibson et al. ................ 203/91 |
| 4,673,762 | A | | 6/1987 | Paslean et al. |
| 6,683,217 | B2 | * | 1/2004 | Brun-Buisson et al. ..... 564/477 |
| 7,164,044 | B2 | * | 1/2007 | Morishita et al. ........... 564/475 |
| 2001/0031897 | A1 | | 10/2001 | Ruider et al. |
| 2004/0127748 | A1 | | 7/2004 | Brun-Buisson et al. |

FOREIGN PATENT DOCUMENTS

JP    62-19558    1/1987

OTHER PUBLICATIONS

Database CAPLUS on STN, Acc. No. 1975:458092, GB 1387573 (Mar. 19, 1975) (abstract).*

* cited by examiner

*Primary Examiner*—Brian J. Davis
(74) *Attorney, Agent, or Firm*—Oblon, Spivak, McClelland, Maier & Neustadt, P.C.

(57) ABSTRACT

Process for separating triethanolamine continuously by distillation from a mixture of monoethanolamine, diethanolamine and triethanolamine together with ethanolamine ethers and water obtained by reaction of ammonia with ethylene oxide in the liquid phase under superatmospheric pressure and at elevated temperature, in which the mixture is distilled in two stages. The low-boiling fraction and the high-boiling fraction are taken off and discharged in the first stage and the intermediate-boiling fraction comprising >99.4% by weight of triethanolamine and <0.2% by weight of diethanolamine is distilled in the second stage. The distillation of the mixture is preferably carried out in a first column and a second column connected to this or in a dividing wall column.

4 Claims, 2 Drawing Sheets

Figure 1:
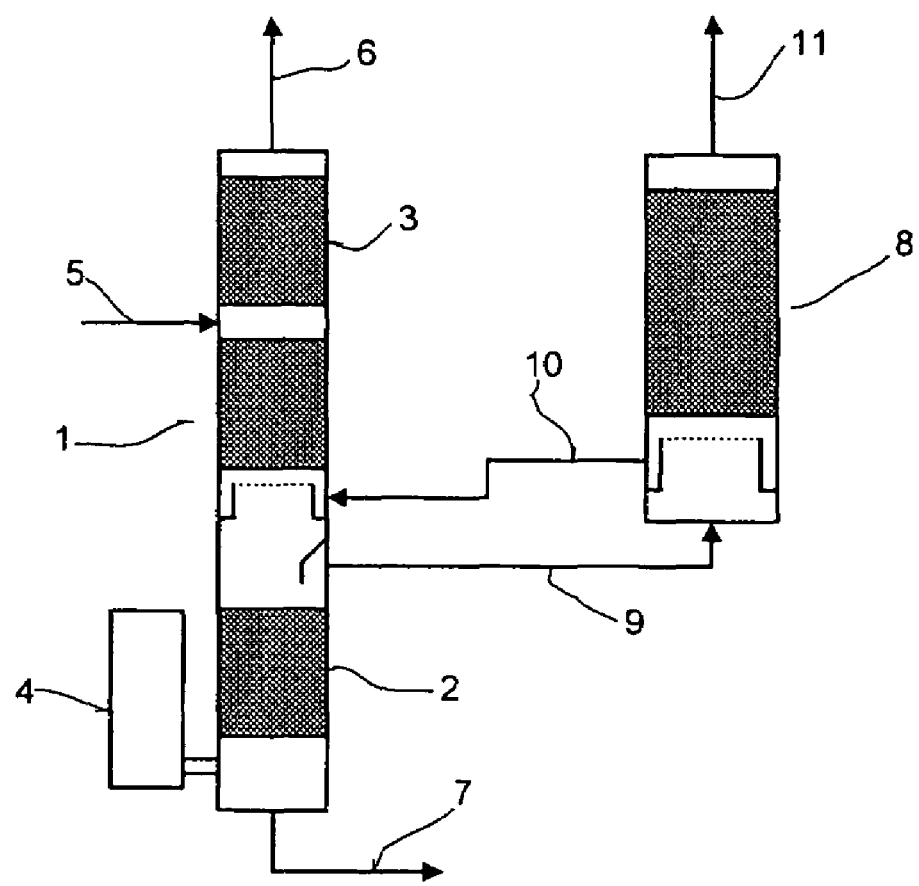

METHOD FOR SEPARATING TRIETHANOLAMIN FROM A MIXTURE OBTAINABLE BY AMMONIA AND ETHYLENE OXIDE REACTION

The present invention relates to a process for separating triethanolamine (TEA) continuously by distillation from a mixture of monoethanolamine, diethanolamine and triethanolamine together with ammonia, water and ethanolamine ethers obtained by reaction of ammonia with ethylene oxide in the liquid phase under superatmospheric pressure and at elevated temperature.

It is generally known that pure, initially colorless TEA (color number: about 0 to 20 APHA in accordance with DIN-ISO 6271 (=Hazen)) obtained after fractional distillation of a crude TEA product which has been obtained by reaction of aqueous ammonia with ethylene oxide and removal of monoethanolamine (MEA) and diethanolamine (DEA) by distillation can gradually become pale pink and finally, especially when allowed to stand in light, yellow to brown after a storage time of from about 4 to 6 weeks, even in closed containers and with exclusion of light. This effect is accelerated by elevated temperatures. (See, for example: G. G. Smirnova et al., J. of Applied Chemistry of the USSR 61, pp. 1508-9 (1988), and Chemical & Engineering News 1996, Sep. 16, page 42, middle column).

According to Chemical & Engineering News 1996, Sep. 16, page 42, one mole of TEA decomposes at elevated temperature to give one mole of ethanolamine and two mole of acetaldehyde. Acetaldehyde condenses to form crotonaldehyde which in turn reacts with ethanolamine to form a Schiff base. This unsaturated Schiff base undergoes 1,4-polymerization to produce colored products in the TEA.

The color quality of pure TEA can be assessed either by time-consuming storage tests in which the APHA color number (in accordance with DIN-ISO 6271) of the TEA is measured as a function of the storage time or, advantageously, by means of the acid neutralization test.

This acid neutralization test allows assessment of the storage stability in color terms of freshly prepared TEA within a few minutes.

The test is described in the Japanese documents JP-A-62 019 558 (Derwent Abstract No. 87-067647/10) and JP-A-62 005 939 (Derwent Abstract No. 87-047397/07), according to which the TEA is treated (neutralized) with acetic acid, citric acid, sulfuric acid, hydrochloric acid or phosphoric acid and the absorbance of the absorption bands at 420 nm and 530 nm is then measured. If no visible pink coloration of the TEA is observed during the test and the measured values of the absorbance remains sufficiently low, the TEA is storage stable in color terms and therefore remains colorless for a period of several months.

Various methods of preparing pure and colorless to only slightly colored TEA are described in the literature.

EP-A-4015 states that ethanolamines having little discoloration are obtained by addition of phosphorous or hypophosphorous acid during the preparation of the ethanolamines and/or the work-up by distillation.

EP-A-36 152 and EP-A-4015 describe the influence of the materials of construction used in processes for preparing alkanolamines on the color quality of the process products and recommend nickel-free or low nickel steels.

U.S. Pat. No. 3,819,710 discloses a process for improving the color quality of ethanolamines by hydrogenation of the crude ethanolamines in the presence of selected catalysts. However, the process is technically complicated and does not lead to a TEA product which remains colorless over a period of months.

U.S. Pat. No. 3,207,790 describes a process for improving the color quality of alkanolamines by addition of a borohydride of an alkali metal.

U.S. Pat. No. 3,742,059 and DE-A-22 25 015 describe the improvement in the color quality of alkanolamines resulting from the addition of an alkanolamine ester of boric acid or alkali metal borates/alkaline earth metal borates.

However, the presence of an auxiliary for stabilizing TEA is undesirable in many important applications of TEA.

The subsequent addition of small amounts of ethylene oxide to freshly distilled TEA likewise leads, according to U.S. Pat. No. 4,673,762, to decolorization and color stabilization. However, the method appears to be problematical for toxicological reasons.

GB-A-1 062 730 describes a process for purifying ethanolamines by distillation in the presence of silicates or aluminates.

JP-A-62 019 558 (Derwent Abstract No. 87-067647/10) reports the preparation of good quality TEA by treatment of crude TEA with inorganic oxides at from 170 to 250° C. and subsequent distillation in the absence of oxygen.

According to JP-A-62 005 939 (Derwent Abstract No. 87-047397/07), similar results are achieved when crude TEA is heated at from 170 to 250° C. for from 1 to 10 hours in the absence of air and is then distilled under reduced pressure.

SU-A-326 178 (Derwent Abstract No. 63384T-AE) describes the preparation of TEA having a good color quality by reaction of anhydrous monoethanolamine (MEA) or diethanblamine (DEA) or mixtures of the two with ethylene oxide under mild conditions at below 50° C.

According to SU-A-228 693 (Chem. Abstr. 70, 77305f (1969)) and GB-A-1 092 449, similar results are achieved when ammonia is reacted with ethylene oxide at ≦35° C. and the resulting ethanolamine mixture is distilled in the absence of air.

From an economic point of view, such processes in which the reactions with ethylene oxide take place at low temperatures are not viable because of the long residence times and the associated low space-time yields.

It is an object of the present invention to provide a process for separating triethanolamine from a mixture obtained by reaction of ammonia with ethylene oxide, by means of which a high purity of the triethanolamine can be achieved. In addition, the preparation of saleable pure triethanolamine should be particularly simple and economical.

We have found that this object is achieved by the measures set forth in claim 1.

Further measures are indicated in the subordinate claims 2 to 4.

The process of the invention uses a mixture which is obtained as follows. Firstly, as described in, for example, EP-A-673 920, an ethanolamine mixture comprising the main components monoethanolamine (MEA), diethanolamine (DEA) and triethanolamine (TEA) is prepared by reaction of aqueous ammonia with ethylene oxide in the liquid phase under superatmospheric pressure and at elevated temperature in a suitable reactor.

The reaction temperatures here are generally from 110 to 180° C., preferably from 120 to 150° C., and the pressures are from 50 to 150 bar (5 to 15 MPa), preferably from 75 to 120 bar (7.5 to 12 MPa). The molar ratio of ammonia to ethylene oxide is from 1:1 to 100:1, preferably from 3:1 to 50:1, particularly preferably from 4:1 to 15:1, and the ammonia is used as a 60-99.99% strength, preferably 70-95% strength, aqueous solution. The ethylene oxide used can be added all at once or in from two to ten, preferably from two to six, portions each amounting to from 10 to 70% by weight of the total amount.

If a molar ratio of ammonia to ethylene oxide of more than 1:1 is employed, the excess ammonia together with part of the water is subsequently distilled off from the resulting product mixture under superatmospheric pressure in a manner known per se and the remaining water is then distilled off under reduced pressure or at atmospheric pressure. This leaves a crude product comprising mostly MEA, DEA and TEA and having a water content of less than 0.3% by weight, preferably less than 0.1% by weight.

After the monoethanolamine (MEA) has subsequently been separated off by distillation under reduced pressure, a crude product comprising DEA, TEA and small amounts of secondary components such as (2-(2-hydroxyethoxy)ethyl) di-(2-hydroxyethyl)amine, (2-(2-hydroxyethoxy)ethyl)(2-hydroxyethyl)amine and N,N'-di-(2-hydroxyethyl)piperazine remains. A typical crude mixture comprises about 70% by weight of DEA and about 30% by weight of TEA.

The composition of this crude product can fluctuate depending on the molar ratio of ammonia to ethylene oxide originally used.

In general, the ethanolamine mixture obtained in this way can be directly subjected to a fractional distillation in which pure DEA and TEA are obtained one after the other. However, an alternative is a procedure in which this crude product which consists essentially of DEA and TEA and has a water content of less than 0.3% by weight, preferably less than 0.1% by weight, and an ammonia content of less than 0.1% by weight, preferably less than 0.01% by weight, is reacted with from 0.6 to 1.2 mol, preferably from 0.8 to 1.1 mol, of ethylene oxide per gram atom of hydrogen bound to nitrogen in the crude product at from 110 to 180° C., preferably from 120° C. to 180° C., in the liquid phase. This reaction is generally carried out as described in GB-A-1 453 762. The reaction is preferably carried out in tube reactors and in a plurality of stages. For example, from 50 to 80% by weight of the ethylene oxide used is reacted in a first reaction stage at preferably from 125 to 165° C., the remainder of the ethylene oxide used is reacted in a second reaction stage at preferably from 150 to 180° C. and the reaction is completed at from 120 to 150° C. in a third reaction stage.

The mixture of MEA, DEA and TEA together with ethanolamine ethers and water obtained in this way is, according to the present invention, distilled in two stages. Conventional distillation apparatuses are suitable for this purpose. Such apparatuses are known to a person skilled in the art. Preference is given to using a distillation column having at least one transverse or longitudinal division configured as a tray, a dividing wall, ordered packing or random packing. The column is advantageously operated at a temperature at the bottom of from 160° C. to 210° C. The pressure selected is in the range from 0.5 mbar to 5 mbar. The column is operated so that a reflux ratio of from 0.05 to 0.5, preferably from 0.1 to 0.4, results. The mixture to be fractionated is preferably fed into the upper half of the column.

To make it possible for the triethanolamine (TEA) to be separated off effectively, the low-boiling fraction is taken off at the top of the column and the high-boiling fraction is taken off at the bottom of the column in a first distillation stage and these fractions are discharged. The remaining intermediate-boiling fraction comprising >98.5% by weight of triethanolamine and <0.2% by weight of diethanolamine is distilled in a second stage.

Owing to the sensitivity of the mixture to heat, it is advantageous to operate the column using a vaporizer which has a low wall temperature and a small liquid capacity. Overall, it has been found to be particularly useful to employ a falling film evaporator. In this case, the bottom of the column and the bottom of the vaporizer are configured so that the residence time of the high-boiling fraction in the bottom of the column is from 1 minute to 60 minutes. At these residence times, an optimum compromise between separation of the intermediate-boiling fraction and avoidance of formation of undesirable by-products is achieved.

In a preferred embodiment of the process of the present invention, the distillation of the mixture is carried out in two connected distillation columns (cf. FIG. 1). Here, the crude TEA mixture to be fractionated is generally fed into the upper part of a first column (1). At the top of this column, a low-boiling fraction is taken off and recirculated to the ethanolamine work-up. At the bottom of column (1), high-boiling components can be discharged if necessary. The intermediate-boiling fraction obtained in the first distillation step is taken off from the column (1) at a side offtake, fed into the lower end of the second distillation stage, viz. column (8), and distilled. It is advantageous for the column (8) also to be provided with at least one transverse or longitudinal division in the form of a tray, a dividing wall, ordered packing or random packing. The high boilers obtained in the column (8) are recirculated to the middle region of column (1). At the top of the second column (8), pure TEA is obtained. The reflux ratio in the column (8) is from 0.2 to 0.7. The first column and the second column are preferably operated using temperature profiles which are approximately the same.

Figure 2:
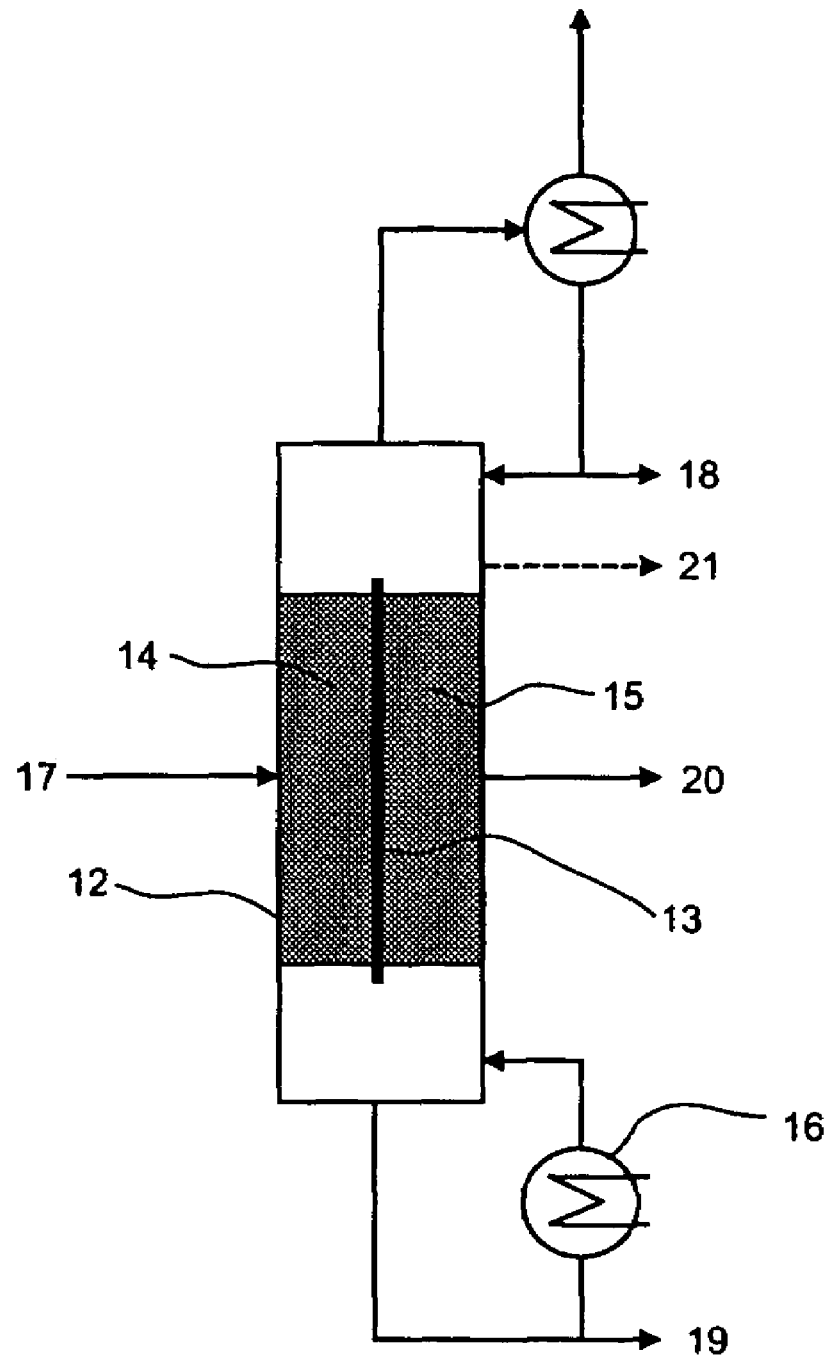

In a particularly advantageous process variant, the distillation of the mixture is carried out in a dividing wall column. A dividing wall column is in principle a simplified form of two thermally coupled distillation columns. It generally contains a vertical dividing wall which extends above and below the feed point and divides the column into an inflow section and an offtake section. To carry out the process of the present invention, the dividing wall column can be configured as a packed column containing random or ordered packing or as a tray column. The mixture is introduced into the column (12) in the middle region of the dividing wall (13) (FIG. 2). The first distillation stage is carried out in the inflow section (14) of the column and the intermediate-boiling fraction remaining after the low-boiling fraction has been taken off at the top of the column and the high-boiling fraction has been taken off at the bottom of the column is distilled in the offtake section (15) of the column, with pure triethanolamine (TEA) being taken off via a side offtake (20) in the middle region of the dividing wall and the high boilers formed in the second distillation stage likewise being discharged at the bottom of the column.

The process of the present invention gives triethanolamine (TEA) having a purity of >99.4% and an APHA color number of ≦30.

TEA of particularly good color quality having colored numbers of ≦20 and a high color stability is obtained when, as described in EP 4015, an effective amount of phosphorous or hypophosphorous acid or derivatives thereof is added before or during the ethanolamine synthesis from ethylene oxide and ammonia or during the work-up of the resulting ethanolamine mixture by distillation. The addition is preferably made only just before the final distillation of the TEA.

If the additive is added after the reaction of ethylene oxide and ammonia in the distillation of the resulting ethanolamines, the amount added is from 0.005 to 2% by weight, based on the sum of the ethanolamines.

The invention is illustrated below by means of examples and with reference to the drawings.

In the drawings,

FIG. 1 schematically shows a plant comprising
(1) a first column comprising
(2) a stripping section and
(3) an enrichment section,
(4) a falling film evaporator,
(5) a feed line into the column,
(6) an overhead offlake,
(7) a bottom offlake and
(8) a second column which is connected via
(9) a first connecting line and
(10) a second connecting line to the first column and
(11) an overhead offlake for taking off pure TEA;

and

FIG. 2 shows
a dividing wall column (12) provided with
a central dividing wall (13) forming
an inflow section (14) and
an offlake section (15),
a falling film evaporator (16),
a feed line into the column (17),
an overhead offlake (18),
a bottom offlake (19),
a side offlake (20) for taking off pure TEA and
a side offlake (21) for taking off a DEA-rich low-boiling stream.

EXAMPLES

Example 1

340 kg/h of a feed mixture comprising 76.4% of TEA, 22.4% of DEA, 1.1% of ethanolamine ethers, 0.02% of water and 0.1% of phosphorous acid are fed in liquid form at an inflow temperature of 180° C. at the point (5) on the first column (1). The column is operated at a pressure at the top of 2 mbar. At the bottom offtake (7) of the column, 50 kg/h of a mixture of 93% of TEA and 6.9% of ethanolamine ethers is discharged at a temperature of 190° C. The residence time of the liquid in the bottom of the column is about 45 minutes. At the overhead offtake (6) of the column, 120 kg/h of a mixture of 67% of DEA, 32.4% of TEA and 0.4% of ethanolamine ethers are discharged and fed back into the starting mixture. The temperature of the stream is 99° C., and the reflux ratio is 0.2. 240 kg/h of a TEA-rich stream are taken off in gaseous form via the first connecting line (9) and fed into the second column (8).

The column (8), which is equipped with mesh packing, is operated at a pressure at the top of 3.5 mbar. The feed mixture flowing into it is at 183° C. The reflux ratio in the column is 0.4. 70 kg/h of a stream taken off via the second connecting line (10) are conveyed back to the first column (1). The stream has a temperature of 179° C. and comprises 98.9% of TEA, 0.4% of DEA and 0.7% of ethanolamine ethers. At the top (11) of this column, 170 kg/h of TEA having a purity of 99.6% are obtained at a temperature of 171° C. The color number of this product is 2 APHA.

Example 2

2300 kg/h of a mixture of 1800 kg of TEA, 490 kg of DEA; 20 kg of ethanolamine ethers, 500 ppm of water and 500 ppm of phosphorous acid are fed into a dividing wall column (12) as shown in FIG. 2 via the feed line (17). The column is operated at a pressure at the top of 3 mbar. The inflow temperature is about 100° C. About 2400 kg/h of a DEA-rich stream are taken off via the overhead offtake (18). About 800 kg/h of this are recirculated to the DEA work-up. The remaining 1600 kg/h are returned to the dividing wall column as runback, with half the amount going to the inflow section (14) and half going to the offtake section (15). About 450 kg/h of high boilers accumulate at the bottom of the column and are discharged at a temperature of 190° C. via the bottom offtake (19). TEA is concentrated in the offtake section (15) of the dividing wall column (12) and is taken off in liquid form at a rate of 1050 kg/h via the side offtake (20). TEA having a purity of 99.5% is obtained. The DEA content is 0.1%.

We claim:

1. A process for separating triethanolamine continuously by distillation from a mixture of monoethanolamine, diethanolamine and triethanolamine together with ethanolamine ethers and water obtained by reaction of ammonia with ethylene oxide in the liquid phase under superatmospheric pressure and at elevated temperature, which comprises distilling the mixture in two stages, where the low-boiling fraction and the high-boiling fraction are taken off and discharged in the first stage and the intermediate-boiling fraction comprising >99.4% by weight of triethanolamine and <0.2% by weight of diethanolamine is distilled in the second stage.

2. A process as claimed in claim 1, wherein the distillation of the mixture is carried out in a first column and a second column connected to this.

3. A process as claimed in claim 1, wherein the distillation of the mixture is carried out in a dividing wall column.

4. A process as claimed in claim 3, wherein the mixture is fed into the column in the middle region of the dividing wall and triethanolamine is discharged from the column.

* * * * *